United States Patent [19]
Halbert

[11] 4,207,245
[45] Jun. 10, 1980

[54] ORGANOMETALLIC INTERCALATES OF METAL CHALCOGENOHALIDES

[75] Inventor: Thomas R. Halbert, Fanwood, N.J.

[73] Assignee: Exxon Research & Engineering Co., Florham Park, Del.

[21] Appl. No.: 67

[22] Filed: Jan. 2, 1979

[51] Int. Cl.$^2$ .............................................. C07F 7/28
[52] U.S. Cl. ................................. 260/429.5; 250/272; 250/475.1; 252/49.7; 252/431 R; 260/429 CY; 260/429.3; 260/438.5 R; 260/439 CY; 429/218; 429/221
[58] Field of Search ................. 260/429 CY, 439 CY, 260/429.3, 429.5, 438.5 R

[56] References Cited

U.S. PATENT DOCUMENTS

| | | | |
|---|---|---|---|
| 3,673,015 | 6/1972 | Sollott et al. | 260/439 CY X |
| 3,688,109 | 8/1972 | Gamble | 260/429 R X |
| 3,980,684 | 9/1976 | Dines | 260/429 CY |
| 4,049,887 | 9/1977 | Whittingham | 429/112 |
| 4,094,893 | 6/1978 | Dines | 260/429 R |
| 4,119,655 | 10/1978 | Hulme | 260/429.3 X |

OTHER PUBLICATIONS

Clement et al, Inorganic Chemistry, 17 2754-2758 (1978).

*Primary Examiner*—Helen M. S. Sneed
*Attorney, Agent, or Firm*—D. W. Collins; J. H. Takemoto

[57] ABSTRACT

A new group of materials comprises intercalates of organometallic compounds in layered structures of metal chalcogenohalides. The organometallic intercalates are represented by the general formula $MX_aY_b[Z]_c$, where M is at least one metal selected from the group consisting of titanium, vanadium, chromium, manganese, iron and indium, X and Y are members of the group consisting of chalcogenides and halides, "a" and "b" each range from 0 to 2, with the sum of "a" and "b" being substantially equal to about 2, Z is an organometallic "sandwich" compound with parallel carbocyclic rings and a first ionization potential less than about 7 eV and "c" ranges from about 0.1 to 0.2.

13 Claims, No Drawings

ORGANOMETALLIC INTERCALATES OF METAL CHALCOGENOHALIDES

BACKGROUND OF THE INVENTION

1. Field of the Invention

The invention is directed to organometallic intercalation compounds.

2. Description of the Prior Art

Organometallic intercalation compounds are disclosed in U.S. Pat. No. 3,980,684. The intercalation compounds are layered structures of metal dichalcogenides and metallocenes. The materials are disclosed as suitable for diffracting soft X-rays with wavelengths as long as about 20 Å.

Organometallic "sandwich" compounds are characterized as those having structures in which a metal ion is situated between two parallel planar carbocyclic 5, 6 or 7 membered rings, the two rings being either the same or different. The metals in such organometallic compounds typically exhibit electropositive characteristics, easily losing an electron to form the corresponding cationic species. The ease of oxidation can be conveniently judged by comparison of the experimentally measured ionization potentials. Some typical organometallic sandwich compounds and corresponding first ionization potentials are listed below:

TABLE I

| Organometallic Compound | First Ionization Potential, eV |
|---|---|
| $Cr(C_6H_6)_2$ | 5.4 |
| $Cr(C_5H_5)_2$ | 5.5 |
| $Ti(C_6H_6)_2$ | 5.5 |
| $Mo(C_6H_6)_2$ | 5.52 |
| $Co(C_5H_5)_2$ | 5.56 |
| $Ti(C_5H_5)(C_7H_7)$ | 5.67 |
| $Mo(C_5H_5)(C_7H_7)$ | 5.87 |
| $Nb(C_7H_7)(C_5H_5)$ | 5.98 |
| $Mn[C_5H_4(CH_3)]_2$ | 6.01 |
| $Ni(C_5H_5)_2$ | 6.2 |
| $Mn(C_5H_5)(C_6H_6)$ | 6.36 |
| $Mn(C_5H_5)_2$ | 6.55 |
| $Fe(C_5H_5)_2$ | 6.88 |
| $Zr(C_5H_5)(C_7H_7)$ | 6.94 |
| $Ru(C_5H_5)_2$ | 7.45 |

Layered metal chalcogenohalides are oxidants; that is, they readily accept electrons and therefore react readily with electropositive species such as alkali metals, simultaneously oxidizing them and intercalating them (inserting the metal ion between layers). The intercalation of layered metal oxyhalides with Group IA, IB, IIA, IIB and IIIA metals is disclosed in U.S. Pat. No. 4,049,887.

SUMMARY OF THE INVENTION

In accordance with the invention, a novel composition of matter comprises intercalates of organometallic "sandwich" compounds in the layered structure of metal chalcogenohalides, the intercalate being represented by the general formula $MX_aY_b[Z]_c$, where M is at least one metal selected from the group consisting of titanium, vanadium, chromium, manganese, iron and indium, X and Y are members of the group consisting of chalcogenides and halides, "a" and "b" each range from 0 to 2, with the sum of "a" and "b" being substantially equal to about 2, Z is an organometallic sandwich compound with parallel carbocyclic rings and a first ionization potential less than about 7 eV and "c" ranges from about 0.1 to 0.2.

DETAILED DESCRIPTION OF THE INVENTION

Intercalation compounds comprise an intercalation host and an intercalated guest. The novel compositions of matter of the invention include as intercalation hosts layered metal chalcogenohalides having the formula $MX_aY_b$, where M is a member selected from the group consisting of iron, vanadium, titanium, chromium, manganese and indium, X and Y are members selected from the group consisting of chalcogenides and halides and "a" and "b" each range from 0 to 2, with the sum of "a" and "b" being substantially equal to about 2. Chalcogenide elements suitable in the practice of the invention include oxygen and sulfur; oxygen is preferred, since metal oxyhalides easily form the desired layered structure. Halide elements suitable in the practice of the invention include chlorine, bromine, and iodine; chlorine is preferred since metal oxychlorides readily formed the desired layered structure. The layered compounds have structures developed from crystallographic space group $V_H13$ according to the Schoenflies system (or Pmnm in the Hermann-Mauguin system). Examples of intercalation hosts suitable in the practice of the invention include FeOCl, VOCl and TiOCl.

The layered metal chalcogenohalides are reacted with an organometallic "sandwich" compound, as described more fully below. The organometallic sandwich compound, Z, is of the form M'LL', where M' is at least one metal selected from the group consisting of titanium, zirconium, vanadium, niobium, chromium, molybdenum, manganese, iron, ruthenium, osmium, cobalt, rhodium, iridium and nickel and L and L' are carbocyclic ligands of the form $C_nH_{n-q}R_q$, where "n" is an integer from 5 to 7, "q" is an integer of between 0 and "n" and R is an organic radical, which may be the same or different for "q" greater than 1, and is selected from the group consisting of $C_1$-$C_2$ linear and $C_3$-$C_{12}$ branched hydrocarbyls, $C_3$-$C_{12}$ cyclic alkyls, $C_2$-$C_{12}$ alkenyls, $C_2$-$C_{12}$ alkoxy, $C_2$-$C_{12}$ alkynyls, $C_6$-$C_{18}$ aryloxy and $C_6$-$C_{18}$ aryls. The ratio of the intercalated organometallic sandwich compound to the metal chalcogenohalide ranges from about 0.1 to 0.2. Examples of organometallic sandwich compounds suitable in the practice of the invention include ferrocene [bis-cyclopentadienyl iron; $Fe(C_5H_5)_2$], cobaltocene [bis-cyclopentadienyl cobalt; $Co(C_5H_5)_2$] and chromocene [bis-cyclopentadienyl chromium; $Cr(C_5H_5)_2$].

An important parameter in the preparation of intercalated organometallic metal chalcogenohalides is the ionization potential of the organometallic "sandwich" compound. That is, the more easily the organometallic compound loses an electron, the more easily an intercalation compound will be formed. It has been found that the organometallic sandwich compounds which interact with metal chalcogenohalides to yield intercalated products are those which possess first ionization potentials of less than about 7 eV.

The upper value of the first ionization potential may vary somewhat, less than about 10%, depending on the particular metal chalcogenohalide. Simple experimentation will readily show whether organometallic compounds having first ionization potentials of about 7 eV will intercalate.

Examples of intercalated compounds within the scope of the invention include the following:
$FeOCl[Fe(C_5H_5)_2]_{0.1-0.2}$ FeOCl[Cr(C$_6$H$_6$)$_2$]$_{0.1-0.2}$
FeOCl[Mo(C$_6$H$_6$)$_2$]$_{0.1-0.2}$
FeOCl[Ti(C$_5$H$_5$)(C$_7$H$_7$)]$_{0.1-0.2}$
FeOCl[Co(C$_5$H$_5$)$_2$]$_{0.1-0.2}$
FeOCl[Mn(C$_5$H$_5$)$_2$]$_{0.1-0.2}$
VOCl[Co(C$_5$H$_5$)$_2$]$_{0.1-0.2}$
VOCl[Cr(C$_5$H$_5$)$_2$]$_{0.1-0.2}$
VOCl[Ti($_6$H$_6$)$_2$]$_{0.1-0.2}$
VOCl[V(C$_6$H$_3$(CH$_3$)$_3$)$_2$]$_{0.1-0.2}$
VOCl[Mo(C$_6$H$_6$)$_2$]$_{0.1-0.2}$
VOCl[Cr(C$_6$H$_6$)$_2$]$_{0.1-0.2}$
CrOCl[Co(C$_5$H$_5$)$_2$]$_{0.1-0.2}$
CrOCl[Fe(C$_5$H$_5$)$_2$]$_{0.1-0.2}$
CrOBr[Co(C$_5$H$_5$)$_2$]$_{0.1-0.2}$
CrOBr[Fe(C$_5$H$_5$)$_2$]$_{0.1-0.2}$
InOCl[CO(C$_5$H$_5$)$_2$]$_{0.1-0.2}$
InOCl[Fe(C$_5$H$_5$)$_2$]$_{0.1-0.2}$
InOBr[Co(C$_5$H$_5$)$_2$]$_{0.1-0.2}$
InOBr[Fe(C$_5$H$_5$)$_2$]$_{0.1-0.2}$
TiOCl[Co(C$_5$H$_5$)$_2$]$_{0.1-0.2}$
TiOCl[Cr(C$_5$H$_5$)$_2$]$_{0.1-0.2}$
TiOCl[Ti(C$_6$H$_6$)$_2$]$_{0.1-0.2}$
TiOCl[V(C$_6$H$_3$(CH$_3$)$_3$)$_2$]$_{0.1-0.2}$
TiOCl[Mo(C$_6$H$_6$)$_2$]$_{0.1-0.2}$
TiOCl[Cr(C$_6$H$_6$)$_2$]$_{0.1-0.2}$ The intercalated compounds of the invention are conveniently prepared by mixing a solution of the organometallic compound in an inert solvent with a solid metal chalcogenohalide. Although the mixing may be done at ambient conditions, it is preferred to heat the solution at temperatures which may range to just below the decomposition temperature of the reactants. Generally, heating in the range of about 80° to 100° C. is sufficient.

The intercalation process is apparently kinetically limited. Reactions typically take about 2 to 30 days to go to completion.

The inert solvent used may be any solvent that is not reduced by the organometallic compound and which does not intercalate in the metal chalcogenohalide host. Examples of suitable solvents include toluene, benzene, and hexane.

The metal chalcogenohalides and the metallocene intercalates decompose in moist air. Accordingly, the reaction is run under an inert atmosphere, such as helium, nitrogen, argon, and the like.

The new compositions of matter are easily characterized as layered compounds by X-ray diffraction. The stoichiometry is established by elemental analysis. These new compositions of matter are useful as catalysts, diffraction gratings, lubricants and battery cathodes.

EXAMPLES

Example 1

A. Synthesis of FeOCl

FeCl$_3$ (MCB Manufacturing Co., anhydrous sublimed) and Fe$_2$O$_3$ (J. T. Baker Chem. Co.) were ground together in a 4/3 molar ratio under inert atmosphere, and sealed in an evacuated quartz tube. The tube was heated at 370°±5° C. for three to four days, and then allowed to cool. The resulting violet microcrystalline mass was removed from the tube under He, and washed with acetone (dried over 4 A molecular sieves) to remove excess FeCl$_3$. The fraction of solid which passed through a 200 mesh sieve was washed again with acetone, and dried under vacuum. Analysis of the powder X-ray diffraction pattern of the product gave the following parameters for the orthorhombic cell: a=3.770, b=7.907, c=3.302.

B. Synthesis of Intercalates

In a typical reaction, FeOCl and the appropriate metallocene were combined in a molar ratio between 1:0.5 and 1:0.1, and loaded under inert atmosphere into a Pyrex Carius tube. Enough toluene was added to dissolve the metallocene, and the tube was cooled in liquid N$_2$, evacuated, sealed, and placed in an oil bath controlled at either 80° or 100° C. When the reaction was judged complete (4 days to 3 weeks), the tube was opened under inert atmosphere, and the solid product filtered, washed with toluene to remove any unreacted metallocene and dried under vacuum. Both the starting FeOCl and the metallocene intercalates decomposed noticeably upon exposure to moist air.

The ferrocene intercalate had stoichiometry FeOCl(ferrocene)$_{0.16}$ as judged by elemental analysis of a sample prepared with 2:1 FeOCl/ferrocene (100° C., 7 days). Lower temperatures or shorter reaction times led to products which evidenced X-ray powder diffraction lines due to both intercalate and unreacted FeOCl. No intermediate phases were observed. The exact stoichiometry of the cobaltocene intercalate was somewhat less certain, because reaction mixtures with greater than 0.15 cobaltocene per FeOCl evidenced some decomposition (indicated by appearance of a blue color in the toluene and degradation of the X-ray diffraction lines), while reaction mixtures with less than or equal to 0.15 cobaltocene per FeOCl, which yielded colorless toluene filtrates, exhibited X-ray diffraction lines due to unreacted FeOCl. However, the relative intensities suggest that the stoichiometry was close to FeOCl(cobaltocene)$_{0.16}$.

C. Results

FeOCl crystallizes in the orthorhombic space group Pmnm. The structure is characterized by layers of distorted edge-shared octahedra, similar to those in γ-FeOOH. Each iron is coordinated to four O$^{2-}$ and two Cl$^-$, with the two Cl$^-$ in cis positions along the outside of the layers. The interlayer Cl$^-$—Cl$^-$ distance of 3.680 Å is approximately twice the Van der Waals radius of chlorine. Thus the only interlayer bonding is due to weak Van Der Waals forces.

Reactions of FeOCl with cobaltocene or ferrocene led to crystalline products, whose nature as intercalation compounds could readily be confirmed. The X-ray powder diffraction data for the cobaltocene intercalate are set forth in Table II; data for the ferrocene intercalate were very similar. In both cases, the data accurately fit an orthorhombic cell, with a and c changed little from FeOCl, and b greatly expanded. Systematic absences suggest a body centered cell. Structural parameters are summarized in Table III. Consideration of these parameters suggests the following simple picture of the intercalation process: In order to accommodate the metallocene, the Van der Waals gap expands by about 5 Å. However, the metallocene also "nests" in the Cl$^-$ layers, and this "nesting" is optimized by a translation of alternate layers of the FeOCl by ½ unit cell along the [101] direction (a, c diagonal). Thus, the translation of alternate layers leads to doubling of the already expanded b parameter, as well as to body-centering of the cell.

TABLE II
X-RAY POWDER DIFFRACTION DATA FOR FeOCl[Co($C_5H_5$)$_2$]$_{0.16}$

| 2θ obs.(a) | I | hkl | d obs (Å) | d calc (Å) |
|---|---|---|---|---|
| 6.85 | >100 | 020 | 12.89 | 12.85 |
| 13.75 | >100 | 040 | 6.435 | 6.423 |
| 23.65 | 24 | 110 | 3.759 | 3.761 |
| 25.58 | 100 | 130 | 3.479 | 3.475 |
| 27.72 | 29 | 080 | 3.215 | 3.211 |
| 29.18 | 19 | 150 | 3.058 | 3.056 |
| 31.95 | 5 | 051 | 2.799 | 2.796 |
| 34.90 | 2 | 0.10.0 | 2.569 | 2.569 |
| 36.35 | 13 | 071 | 2.469 | 2.467 |
| 38.50 | 26(b) | 141 | 2.336 | 2.335 |
| 39.42 | 2 | 190 | 2.284 | 2.283 |
| 41.60 | 7 | 091 | 2.169 | 2.168 |
| 42.20 | 5 | 0.12.0 | 2.140 | 2.141 |
| 45.52 | 4 | 1.11.0 | 1.9910 | 1.9900 |
| 45.90 | 2 | 181 | 1.9753 | 1.9757 |
| 47.50 | 3 | 0.11.1 | 1.9125 | 1.9125 |
| 47.83 | 14 | 200 | 1.9000 | 1.9011 |
| 48.38 | 9 | 220 | 1.8797 | 1.8806 |
| 49.65 | 18 | 0.14.0 | 1.8346 | 1.8350 |
| 50.83 | 5 | 1.10.1 | 1.7947 | 1.7939 |
| 52.10 | 2 | 1.13.0 | 1.7539 | 1.7535 |
| 55.10 | 1 | 002 | 1.6653 | 1.6662 |
| 56.40 | 2 | 1.12.1 | 1.6321 | 1.6278 |
| 57.33 | 7 | 0.16.0 | 1.6057 | 1.6056 |
| 58.64 | 2 | 251 | 1.5729 | 1.5721 |
| 61.55 | 5 | 271 | 1.5054 | 1.5059 |
| 65.20 | 7(b) | 291 | 1.4296 | 1.4293 |
| 66.55 | 3 | 1.17.0 | 1.4039 | 1.4043 |
| 71.35 | 1 | 2.14.0 | 1.3208 | 1.3203 |
| 74.35 | 1 | 1.19.0 | 1.2747 | 1.2740 |
| 75.80 | 1 | 330 | 1.2539 | 1.2537 |
|  |  | 0.19.1 |  | 1.2529 |
| 82.70 | 1(b) | 341 | 1.1659 | 1.1655 |
|  |  | 1.21.0 |  | 1.1652 |

(a) Cu Kα radiation
(b) Al interference

TABLE III
SUMMARY OF STRUCTURAL PARAMETERS

|  | a | b | c | Layer Expansion (Å) |
|---|---|---|---|---|
| FeOCl | 3.770 | 7.907 | 3.302 | — |
| FeOCl[Co($C_5H_5$)$_2$]$_{0.16}$ | 3.803 | 25.698 (2 × 12.849) | 3.335 | 4.94 |
| FeOCl[Fe($C_5H_5$)$_2$]$_{0.16}$ | 3.792 | 26.064 (2 × 13.032) | 3.324 | 5.13 |

EXAMPLE 2

A mixture of 0.25 g FeOCl (−200 mesh, 2.34 meq), 9.90 g cobaltocene (0.476 meq) and 3 ml toluene were placed in a Pyrex Carius tube under inert atmosphere of helium. The tube was cooled in liquid nitrogen, evacuated and sealed. After five days in an oil bath at 80°±2° C., the supernatant was nearly clear, indicating that the cobaltocene had intercalated. The resulting black microcrystalline solid was filtered and dried under inert atmosphere of helium. X-ray powder diffraction demonstrated that intercalation had occurred.

EXAMPLE 3

A mixture of 0.254 g FeOCl (2.36 meq), 0.127 g ferrocene (0.683 meq) and 3 ml of toluene were placed in a Pyrex Carius tube under inert atmosphere of helium. The tube was cooled in liquid nitrogen, evacuated and sealed. After 24 days in an oil bath at 80°±2° C., the yellow-orange supernatant was filtered off under inert atmosphere of helium, leaving the product as a dark, black-violet microcrystalline solid (0.299 g). X-ray powder diffraction demonstrated that intercalation had occurred.

EXAMPLE 4

A mixture of 0.25 g VOCl (−200 mesh, 2.44 meq), 0.114 g cobaltocene (0.60 meq) and 3 ml of toluene were placed in a Pyrex Carius tube under inert atmosphere of helium. The tube was cooled in liquid nitrogen, evacuated and sealed. After 15 days in an oil bath at 100°±2° C., the tube was cooled, opened under inert atmosphere of helium, and the resulting black microcrystalline solid was filtered and dried. X-ray powder diffraction indicated that intercalation had occurred.

EXAMPLE 5

A mixture of 0.25 g TiOCl (2.52 meq), 0.12 g cobaltocene (0.66 meq) and 3 ml of toluene were placed in a Pyrex Carius tube under inert atmosphere of helium. The tube was cooled in liquid nitrogen, evacuated and sealed. After 90 days in an oil bath at 100°±2° C., the tube was cooled, opened under inert atmosphere of helium, and the resulting brown-black microcrystalline solid filtered and dried. X-ray powder diffraction indicated that intercalation had occurred.

What is claimed is:

1. A composition of matter comprising an organometallic sandwich compound intercalated in the layered structure of a metal chalcogenohalide, the composition being represented by the general formula $MX_aY_b[Z]_c$, where M is at least one metal selected from the group consisting of titanium, vanadium, chromium, manganese, iron and indium, X is a chalcogenide, Y is a halide, the sum of "a" and "b" is substantially equal to about 2, Z is an organometallic sandwich compound with parallel carbocyclic rings and a first ionization potential of less than about 7 eV and "c" ranges from about 0.1 to 0.2, where in the layered metal chalcogenohalide belongs to orthohombic space group Pnmn.

2. The composition of claim 1 in which M is selected from the group consisting of titanium, vanadium, iron, and chromium.

3. The composition of claim 1 in which X is oxygen.

4. The composition of claim 1 in which Y is chlorine.

5. The composition of claim 1 in which the metal chalcogenohalide is selected from the group consisting of FeOCl, VOCl and TiOCl.

6. The composition of claim 1 in which Z is given by the formula M'LL', where M' is at least one metal selected from the group consisting of titanium, zirconium, vanadium, niobium, chromium, molybdenum, manganese, iron, ruthenium, osmium, cobalt, rhodium, iridium and nickel and L and L' are carbocyclic ligands of the form $C_nC_{n-q}R_q$, where "n" is an integer from 5 to 7, "q" is an integer between 0 and "n" and R is an organic radical, which may be the same or different for "q" greater than 1, and is selected from the group consisting of $C_1$–$C_2$ linear and $C_3$–$C_{12}$ branched hydrocarbyls, $C_3$–$C_{12}$ cyclic alkyls, $C_2$–$C_{12}$ alkenyls, $C_2$–$C_{12}$ alkynyls, $C_6$–$C_{18}$ aryloxy and $C_6$–$C_{18}$ aryls.

7. The composition of claim 6 in which the organometallic compound is selected from the group consisting of Fe($C_5H_5$)$_2$, Co($C_5H_5$)$_2$ and Cr($C_5H_5$)$_2$.

8. The composition of claim 1 having the formula FeOCl[Fe($C_5H_5$)$_2$]$_c$.

9. The composition of claim 8 in which "c" is about 0.16.

10. The composition of claim 1 having the formula $FeOCl[Co(C_5H_5)_2]_c$.

11. The composition of claim 10 in which "c" is about 0.16.

12. The composition of claim 1 having the formula $VOCl[Co(C_5H_5)_2]_c$.

13. The composition of claim 1 having the formula $TiOCl[Co(C_5H_5)_2]_c$.

* * * * *